(12) United States Patent
Nishiguchi et al.

(10) Patent No.: US 8,877,989 B2
(45) Date of Patent: Nov. 4, 2014

(54) DEHYDRATION PROCESS OF HYDROFLUOROCARBON OR HYDROCHLOROFLUOROCARBON AND PRODUCTION METHOD OF 1,3,3,3-TETRAFLUOROPROPENE USING THE DEHYDRATION PROCESS

(75) Inventors: Yoshio Nishiguchi, Iruma-gun (JP);
Yasuo Hibino, Shiki (JP)

(73) Assignee: Central Glass Company, Limited, Ube-shi (JP)

( * ) Notice: Subject to any disclaimer, the term of this patent is extended or adjusted under 35 U.S.C. 154(b) by 77 days.

(21) Appl. No.: 13/188,884

(22) Filed: Jul. 22, 2011

(65) Prior Publication Data

US 2012/0065435 A1 Mar. 15, 2012

(30) Foreign Application Priority Data

Sep. 14, 2010 (JP) .................................. 2010-205473
Jun. 30, 2011 (JP) .................................. 2011-145451

(51) Int. Cl.
*C07C 17/08* (2006.01)
*C07C 17/25* (2006.01)
*C07C 17/383* (2006.01)
*C07C 17/20* (2006.01)
*C07C 17/21* (2006.01)
*C07C 17/38* (2006.01)

(52) U.S. Cl.
CPC ............. *C07C 17/38* (2013.01); *C07C 17/25* (2013.01); *C07C 17/383* (2013.01); *C07C 17/206* (2013.01); *C07C 17/21* (2013.01)
USPC ........................................................ 570/164

(58) Field of Classification Search
None
See application file for complete search history.

(56) References Cited

U.S. PATENT DOCUMENTS

| 3,793,801 A | 2/1974 | Tsao |
| 4,932,984 A | 6/1990 | Nankee |
| 5,679,875 A | 10/1997 | Aoyama et al. |

(Continued)

FOREIGN PATENT DOCUMENTS

| CN | 101293809 A | 10/2008 |
| GB | 1 533 303 | 11/1978 |

(Continued)

OTHER PUBLICATIONS

International Search Report including partial English Translation dated Aug. 2, 2011 (Eight (8) pages.

(Continued)

*Primary Examiner* — Clinton Brooks
(74) *Attorney, Agent, or Firm* — Crowell & Moring LLP (57) ABSTRACT

A process for dehydrating a hydrofluorocarbon or hydrochlorofluorocarbon, which can be done by simple equipment, and a continuous process of producing 1,3,3,3-tetrafluoropropene using the dehydration process. The dehydration process includes cooling the hydrofluorocarbon or hydrochlorofluorocarbon in gaseous form containing water with a heat exchanger, thereby condensing and liquefying the hydrofluorocarbon or hydrochlorofluorocarbon while freezing and solidifying the water. The 1,3,3,3-tetrafluoropropene production method includes a first step for fluorinating 1-chloro-3,3,3-trifluoropropene with hydrogen fluoride to obtain a mixture of 1,3,3,3-tetrafluoropropene, unreacted 1-chloro-3,3,3-trifluoropropene, hydrogen fluoride, hydrogen chloride and by-products, or dehydrofluorinating 1,1,1,3,3-pentafluoropropane to obtain a mixture of 1,3,3,3-tetrafluoropropene, unreacted 1,1,1,3,3-pentafluoropropane and by-products, a second step for removing acidic components, a third step for dehydrating the 1,3,3,3-tetrafluoropropene by the above dehydration process, and a fourth step for purifying the 1,3,3,3-tetrafluoropropene by distillation.

11 Claims, 1 Drawing Sheet

(56) References Cited

U.S. PATENT DOCUMENTS

| | | |
|---|---|---|
| 6,375,808 B1 | 4/2002 | Tsuda et al. |
| 6,472,573 B1 * | 10/2002 | Yamamoto et al. ........... 570/164 |
| 7,543,456 B2 * | 6/2009 | Sinha et al. ................. 62/238.6 |
| 7,638,660 B2 * | 12/2009 | Wang et al. ................... 570/236 |

FOREIGN PATENT DOCUMENTS

| | | |
|---|---|---|
| JP | 49-70906 | 7/1974 |
| JP | 52-7381 | 1/1977 |
| JP | 62-135437 A | 6/1987 |
| JP | 3-66633 A | 3/1991 |
| JP | 9-241189 A | 9/1997 |
| JP | 10-7604 A | 1/1998 |
| JP | 11-140002 A | 5/1999 |
| JP | 3158440 B2 | 2/2001 |
| JP | 2002-126402 A | 5/2002 |
| JP | 2004-43410 A | 2/2004 |
| JP | 2010-83818 A | 4/2010 |
| JP | 2010-100613 A | 5/2010 |
| WO | WO 98/08789 A1 | 3/1998 |
| WO | WO 2010/035748 A1 | 4/2010 |

OTHER PUBLICATIONS

PCT/ISA/237 Form (Four (4) pages), 2011.

R.N. Haszeldine et al., "The Addition of Free Radicals to Unsaturated Systems", J.Chem. Soc., 1953, pp. 1199-1206, Part 2.

I.L. Knunyants et al., "Catalytic Hydrogenation of Perfluoro Olefins", Institute of Heteroorganic Compounds, Academy of Sciences of the USSR, Aug. 1960, No. 8, Communication 13, pp. 1312-1317.

Translation of JP 62-135437 A (seven (7) pages), 1987.

* cited by examiner

DEHYDRATION PROCESS OF HYDROFLUOROCARBON OR HYDROCHLOROFLUOROCARBON AND PRODUCTION METHOD OF 1,3,3,3-TETRAFLUOROPROPENE USING THE DEHYDRATION PROCESS

FIELD OF THE INVENTION

The present invention relates to a dehydration process of a hydrofluorocarbon or hydrochlorofluorocarbon and more particularly to, as an application example of the dehydration process, a production method of 1,3,3,3-tetrafluoropropene that is useful as a blowing agent, a coolant, an intermediate raw material for pharmaceutical and agrichemical products, a propellant for aerosols such as a spray or a protection gas for production of magnesium alloys.

BACKGROUND ART

The following processes are known as methods for production of 1,3,3,3-tetrafluoropropene that is one kind of fluoroolefin.

For example, Non-Patent Document 1 discloses a process of dehydroiodination of 1,3,3,3-tetrafluoro-1-iodopropane with alcoholic potassium hydroxide.

Patent Document 1 discloses a process of production of 1,3,3,3-tetrafluoropropene by reaction of 1-chloro-3,3,3-trifluoropropene ($CF_3CH=CHCl$) with hydrogen fluoride in the presence of a fluorination catalyst, wherein the fluorination catalyst is an activated carbon supporting thereon an oxide, a fluoride, a chloride, a fluorochloride, an oxyfluoride, an oxychloride or an oxyfluorochloride of one kind of metal, or two or more kinds of metals, selected from the group consisting of chromium, titanium, aluminum, manganese, nickel and cobalt.

Patent Document 2 discloses a process of production of 1,3,3,3-tetrafluoropropene by reaction of 1-chloro-3,3,3-trifluoropropene with hydrogen fluoride in the presence of a fluorination catalyst, wherein at least either one of titanium and chromium is used as the fluorination catalyst.

Non-Patent Document 2 discloses a process of dehydrofluorination of 1,1,1,3,3-pentafluoropropane with potassium hydroxide.

Patent Document 3 discloses a process of producing 1,3,3,3-tetrafluoropropene continuously from 1,1,1,3,3-pentafluoropropane by passing the 1,1,1,3,3-pentafluoropropane through a reaction region of carbon material or metal-compound-supported carbon material at an elevated temperature in a gas phase.

Patent Document 4 discloses a process of production of 1,3,3,3-tetrafluoropropene, including: a first step of forming 1-chloro-3,3,3-trifluoropropene by reaction of 1,1,1,3,3-pentachloropropane with hydrogen fluoride; and a second step of reacting the 1-chloro-3,3,3-trifluoropropene obtained in the first step with hydrogen fluoride in a gas phase in the presence of a fluorination catalyst.

Patent Document 5 discloses a process of production of 1,3,3,3-tetrafluoropropene by dehydrofluorination of gaseous 1,1,1,2,3,3-hexafluoropropane by contact with an activated carbon, and then, dehydrofluorination of the resulting gaseous 1,1,1,2,3-pentafluoropropane by contact with a metal-salt-doped activated carbon.

In the production of 1,3,3,3-tetrafluoropropene, the product of the reaction process generally contains not only the 1,3,3,3-tetrafluoropropene and the impurities such as the raw material compound and by-products but also the acidic component as mentioned above. Thus, there is a need to perform an acid removal process so as to remove the acidic component by washing operation, i.e., washing the reaction product with water or aqueous basic solution. When the reaction product contains hydrofluoric acid, it is desirable to bring the reaction product into contact with concentrated sulfuric acid etc. and absorb the hydrofluoric acid by the concentrated sulfuric acid etc.

It is also common practice, in the production of 1,3,3,3-tetrafluoropropene, to continuously perform a distillation process on the 1,3,3,3-tetrafluoropropene containing the impurities such as the unreacted raw material, by-products and entrained water after the acid removal process (hereinafter sometimes referred to as "crude 1,3,3,3-tetrafluoropropene") so as to remove the impurities and purify the 1,3,3,3-tetrafluoropropene.

When the crude 1,3,3,3-tetrafluoropropene contains water, the distillation process faces the problems that: the impurities are difficult to remove; and the water remains in the 1,3,3,3-tetrafluoropropene by the formation of an azeotropic mixture of the 1,3,3,3-tetrafluoropropene and water. For stable, continuous distillation operation, the crude 1,3,3,3-tetrafluoropropene containing the impurities such as the unreacted raw material, by-products etc. needs to be dehydrated sufficiently and then fed continuously to distillation equipment such as a distillation column. It is thus preferable to perform a dehydration process after the acid removal process and before the distillation process, that is, between the acid removal process and the distillation process. It is also preferable, in a plant as an industrial facility for commercial production of 1,3,3,3-tetrafluoropropene, to adopt a simple and efficient dehydration process that does not require large-scale equipment. For example, one conceivable way is to perform a dehydration process and, after the dehydration process, temporarily store in a tank the crude 1,3,3,3-tetrafluoropropene that does not at least contain water but contains the other impurities such as the unreacted raw material and by-products so that the 1,3,3,3-tetrafluoropropene can be fed stably to the subsequent distillation equipment for stable plant operation.

Patent Document 6 discloses, in the production of the 1,3,3,3-tetrafluoropropene, a process of dehydration of 1,3,3,3-tetrafluoropropene containing water after washing with water or aqueous basic solution by contact with a specific kind of zeolite.

Patent Document 7 discloses, in the production of 1,1,1,3,3-pentafluoropropane, a process of dehydration of the 1,1,1,3,3-pentafluoropropane containing water after washing with water or aqueous basic solution by contact with a specific kind of zeolite.

PRIOR ART DOCUMENTS

Patent Document 1: Japanese Laid-Open Patent Publication No. 10-007604
Patent Document 2: Japanese Laid-Open Patent Publication No. 2004-043410
Patent Document 3: Japanese Laid-Open Patent Publication No. 11-140002
Patent Document 4: Japanese Laid-Open Patent Publication No. 2010-100613
Patent Document 5: Japanese Patent No. 3158440
Patent Document 6: Japanese Laid-Open Patent Publication No. 2010-083818
Patent Document 7: Japanese Laid-Open Patent Publication No. 09-241189
Non-Patent Document 1: R. N. Haszeldine et al., J. Chem. Soc. 1953, 1199-1206; CA 48 5787f Non-Patent Document 2: I. L. Knunyants et al., Izvest. Akad. Nauk S.S.S.R., Otdel. Khim. Nauk. 1960, 1412-18; CA 55, 349f

SUMMARY OF THE INVENTION

The dehydration process of Patent Document 6, in which the 1,3,3,3-tetrafluoropropene is brought into contact with the specific kind of zeolite, is superior in that it can be done regardless of whether the 1,3,3,3-tetrafluoropropene is in gaseous form or liquid form. I the case where the gaseous 1,3,3, 3-tetrafluoropropene (hereinafter sometimes referred to as "1,3,3,3-tetrafluoropropene gas") containing water vapor at a water content of 1000 ppm or more after the acid removal process is dehydrated by means of a zeolite-packed dehydration column according to the dehydration process of Patent Document 6, it is necessary to increase the mass flow rate of such water-containing 1,3,3,3-tetrafluoropropene gas through the dehydration column per unit time to a level appropriate for industrial production due to the fact that 1,3,3,3-tetrafluoropropene is generally 230 times larger in volume in gaseous form than in liquid form. However, the capacity of the dehydration column needs to be increased with the mass flow rate of the 1,3,3,3-tetrafluoropropene gas. This leads to the problems that: the zeolite has to be used in a large amount as the dehydration agent and has to be regenerated.

It is therefore an object of the present invention to provide a dehydration process of a hydrofluorocarbon or hydrochlorofluorocarbon, which can be done by simple equipment without the need for large-scale equipment and can suitably be applied for industrial commercial production in a plant. In particular, it is an object of the present invention to provide a continuous production method of 1,3,3,3-tetrafluoropropene by the adoption of the above dehydration process for dehydration of 1,3,3,3-tetrafluoropropene that is one kind of hydrofluorocarbon.

For dehydration of a water-containing gas by cooling and drying, commonly adopted is a dehydration process that involves condensation of water vapor into a liquid by cooling and removal of the resulting liquid water. However, it has not been well known about the industrial process that performs dehydration operation on a water-containing gas to freeze water vapor and remove the frozen water simultaneously with condensation of the gas. In particular, in the fields of industrial production of a low-boiling hydrofluorocarbon or hydrochlorofluorocarbon, there has been known no process of dehydrating a hydrofluorocarbon or hydrochlorofluorocarbon gas containing excessive water vapor by condensation simultaneously with removing the water vapor by freezing, and then, purifying the hydrofluorocarbon or hydrochlorofluorocarbon as the target product.

The present invention was made to solve the above problems. It has been found by the present inventors that, even when a hydrofluorocarbon or hydrochlorofluorocarbon contains water in an amount larger than or equal to the saturated water content, it is possible to dehydrate the hydrofluorocarbon or hydrochlorofluorocarbon to almost no water content by cooling the hydrofluorocarbon or hydrochlorofluorocarbon by a heat exchanger, freezing the water vapor onto a heat transfer surface of the heat exchanger and thereby condensing and extracting only the hydrofluorocarbon or hydrochlorofluorocarbon. Based on this finding, there has been accomplished a dehydration process of a hydrofluorocarbon or hydrochlorofluorocarbon according to the present invention. There has also been accomplished a method for continuous production of 1,3,3,3-tetrafluoropropene by the adoption of the above dehydration process for dehydration of the 1,3,3, 3-tetrafluoropropene.

Namely, the present invention includes the following inventive aspects 1 to 13.

[Inventive Aspect 1]
A dehydration process of a hydrofluorocarbon or hydrochlorofluorocarbon, comprising: cooling the hydrofluorocarbon or hydrochlorofluorocarbon in gaseous form containing at least water by a heat exchanger, thereby condensing and liquefying the hydrofluorocarbon or hydrochlorofluorocarbon while freezing and solidifying the water.

[Inventive Aspect 2]
The dehydration process according to Inventive Aspect 1, wherein the heat exchanger is an indirect heat exchanger.

[Inventive Aspect 3]
The dehydration process according to Inventive Aspect 1, wherein the heat exchanger is of either double-tube type, multi-cylinder type, cylindrical coil type or cylindrical jacketed type.

[Inventive Aspect 4]
The dehydration process according to any one of Inventive Aspects 1 to 3, wherein the hydrofluorocarbon is 1,3,3,3-tetrafluoropropene.

In other words, the present dehydration process includes the step of cooling the 1,3,3,3-tetrafluoropropene containing in gaseous form containing at least water by the heat exchanger, thereby condensing and liquefying the 1,3,3,3-tetrafluoropropene while freezing and solidifying the water.

[Inventive Aspect 5]
The dehydration process according to Inventive Aspect 4, wherein the 1,3,3,3-tetrafluoropropene in gaseous form containing at least water is that formed by fluorination of 1-chloro-3,3,3-trifluoropropene with hydrogen fluoride and then subjected to washing.

[Inventive Aspect 6]
The dehydration process according to Inventive Aspect 5, wherein the 1,3,3,3-tetrafluoropropene contains at least a cis-isomer or a trans-isomer, or a mixture of cis- and trans-isomers, of the 1-chloro-3,3,3-trifluoropropene.

[Inventive Aspect 7]
The dehydration process according to Inventive Aspect 4, wherein the 1,3,3,3-tetrafluoropropene in gaseous form containing at least water is that formed by dehydrofluorination of 1,1,1,3,3-pentafluoropropane and then subjected to washing and contains impurities.

[Inventive Aspect 8]
The dehydration process according to Inventive Aspect 7, wherein the 1,3,3,3-tetrafluoropropene contains at least the 1,1,1,3,3-pentafluoropropane as the impurity.

[Inventive Aspect 9]
The dehydration process according to any one of Inventive Aspects 4 to 8, wherein the 1,3,3,3-tetrafluoropropene is in the form of a cis-isomer or a trans-isomer or a mixture of cis- and trans-isomers thereof.

[Inventive Aspect 10]
A production method of 1,3,3,3-tetrafluoropropene, comprising: a dehydration step of dehydrating 1,3,3,3-tetrafluoropropene by the dehydration process according to any one of Inventive Aspects 1 to 9; and a distillation purification step of distillating and purifying the dehydrated 1,3,3,3-tetrafluoropropene containing impurities.

[Inventive Aspect 11]
The production method according to Inventive Aspect 10, further comprising: a synthesis step for fluorinating 1-chloro-3,3,3-trifluoropropene with hydrogen fluoride to obtain a mixture of the 1,3,3,3-tetrafluoropropene, unreacted 1-chloro-3,3,3-trifluoropropene, hydrogen fluoride, hydrogen chloride and by-products; and an acid removal step for removing the hydrogen fluoride and hydrogen chloride from the mixture.

[Inventive Aspect 12]

The production method according to Inventive Aspect 10, further comprising: a synthesis step for dehydrofluorinating 1,1,1,3,3-pentafluoropropane to obtain a mixture of the 1,3, 3,3-tetrafluoropropene, unreacted 1,1,1,3,3-pentafluoropropane and by-products; and an acid removal step for removing hydrogen fluoride from the mixture.

[Inventive Aspect 13]

The production method according to Inventive Aspect 11 or 12, wherein, in the acid removal step, the hydrogen fluoride is removed by contact of the mixture obtained in the synthesis step with sulfuric acid, water or aqueous basic solution.

The dehydration process of the present invention enables freezing and removing the water contained in the crude hydrofluorocarbon or hydrochlorofluorocarbon by the use of the heat exchanger simultaneously with condensing the hydrofluorocarbon or hydrochlorofluorocarbon. It is therefore possible, as compared to a conventional dehydration process using a dehydration column packed with a zeolite, to achieve not only size reduction and simplification of dehydration equipment but also easy dehydration operation in the dehydration process of the hydrofluorocarbon or hydrochlorofluorocarbon.

Particularly, in a plant, even when the crude hydrofluorocarbon or hydrochlorofluorocarbon gas is subjected to washing to remove the acidic component such as hydrogen fluoride so that water is contained in the crude hydrofluorocarbon or hydrochlorofluorocarbon gas in an amount larger than or equal to the saturated water content, it is possible to dehydrate such a crude hydrofluorocarbon or hydrochlorofluorocarbon gas to almost no water content by cooling the crude hydrofluorocarbon or hydrochlorofluorocarbon gas by the heat exchanger, freezing the water vapor onto a heat transfer surface of the heat exchanger and thereby condensing and extracting the hydrofluorocarbon or hydrochlorofluorocarbon and the impurities such as unreacted raw material and by-products. This contributes to a load reduction of distillation purification operation in the distillation process subsequent to the dehydration process.

The dehydration process of the present invention can suitably be applied for industrial commercial production of 1,3, 3,3-tetrafluoropropene in a plant and enables continuous production of 1,3,3,3-tetrafluoropropene.

DETAILED DESCRIPTION

The present invention provides a dehydration process of a hydrofluorocarbon or hydrochlorofluorocarbon, characterized by including the step of cooling the hydrofluorocarbon or hydrochlorofluorocarbon in gaseous form containing at least water by a heat exchanger, thereby condensing and liquefying the hydrofluorocarbon or hydrochlorofluorocarbon while freezing and solidifying the water, so as to separate and remove the water from the hydrofluorocarbon or hydrochlorofluorocarbon.

Specific examples of the hydrofluorocarbon are fluoromethane, difluoromethane, trifluoromethane, fluoroethane, 1,1-difluoroethane, 1,1,1-trifluoroethane, 1,1,1,2-tetrafluoroethane, pentafluoroethane, 1,1,1,3,3-pentafluoropropane, 1,1,1,3,3,3-hexafluoropropane, 1,1,1,2,3,3,3-heptafluoropropane, 1,1,1,3,3-pentafluorobutane, 3,3,3-trifluoropropene, 2,3,3,3-tetrafluoropropene, 1,3,3,3-tetrafluoropropene or 1,2,3,3,3-pentafluoropropene. Specific examples of the hydrochlorofluorocarbon are chlorodifluoromethane, 1,1-dichloro-2,2,2-trifluoroethane, 1,1-dichloro-1-fluoroethane, 1-chloro-1,1-difluoroethane, 1-chloro-3,3,3-trifluoropropene or 2-chloro-3,3,3-trifluoropropene.

Further, the dehydration process of the present invention can be applied for production of a perfluorocarbon such as tetrafluoromethane, hexafluoroethane, octafluoropropane, tetrafluoroethylene or hexafluoropropene.

The dehydration process of the present invention will be hereinafter described below in detail by taking, as an example, 1,3,3,3-tetrafluoropropene that is one kind of hydrofluorocarbon useful as a blowing agent, a coolant, an intermediate raw material for pharmaceutical and agrichemical products, a propellant for aerosols such as a spray or a protection gas for production of magnesium alloys. A production method of 1,3,3,3-tetrafluoropropene using the dehydration process of the present invention will also be described below.

1. Dehydration Process (Heat Exchanger and its Dehydration Operations)

In the dehydration process of the present invention, there can suitably be used, as the heat exchanger for freezing and removal of the water, an indirect heat exchanger that allows heat exchange between a cooling medium and 1,3,3,3-tetrafluoropropene via a cooling heat transfer surface.

In the case of using a double-tube indirect heat exchanger, for example, it is feasible by flowing a cooling medium through either one of inner and outer tubes of the heat exchanger while flowing a gas containing 1,3,3,3-tetrafluoropropene and water through the other of the inner and outer tubes of the heat exchanger to condensate the 1,3,3,3-tetrafluoropropene and impurities, freeze the water vapor and mist and thereby achieve freeze separation of the water vapor and mist. At this time, the heat exchange efficiency of the heat exchanger can be improved by packing a packing material of high thermal conductivity in the portion of the heat exchanger through which the 1,3,3,3-tetrafluoropropene flows and by attaching a fin to the side of the heat transfer surface with which the 1,3,3,3-tetrafluoropropene comes into contact for increase of effective heat transfer surface area.

Examples of the indirect heat exchanger are those of not only double-tube type but also cylindrical multi-tube type, cylindrical coil type and cylindrical jacketed type. In the dehydration process of the present invention, the cylindrical multi-tube heat exchanger or cylindrical coil heat exchanger may be equipped with an external jacket for increase of heat transfer surface area.

It is preferable to use a metal of high thermal conductivity as the material of the heat exchanger in the dehydration process of the present invention. Examples of such a metal material are iron, iron steel, copper, lead, zinc, brass, stainless steel, titanium, aluminum, magnesium, Monel, Inconel and Hastelloy. For the purpose of corrosion prevention, it is preferable to apply a lining of resin such as fluoro resin, ceramic or glass to the surface of the heat exchanger with which the 1,3,3,3-tetrafluoropropene comes into contact.

It is also preferable that the heat transfer surface area of the heat exchanger is enough to exchange a sufficient amount of heat required for condensation of the gaseous 1,3,3,3-tetrafluoropropene containing at least water and for freezing of the water although the heat transfer surface area of the heat exchanger depends on the temperature of the cooling medium used in the dehydration process of the present invention. In view of the fact that the heat transfer coefficient of the heat exchanger becomes decreased by adhesion of water to the heat transfer surface of the heat exchanger, the heat transfer surface area of the heat exchanger is preferably at least 1.5 times or larger than its theoretically required value. As mentioned above, the fin may be attached to the heat transfer surface of the heat exchanger. It is particularly effective for improvement in heat transfer efficiency to attach the fin to the side of the heat transfer surface with which the 1,3,3,3-tetrafluoropropene comes into contact so as to thereby change the flow of the gas and increase the heat transfer surface area of the heat exchange.

For the introduction of the 1,3,3,3-tetrafluoropropene into the heat exchanger in the dehydration process of the present invention, there can be adopted a flow system that allows the gaseous 1,3,3,3-tetrafluoropropene to flow through the heat exchanger of sufficient heat transfer surface. In the case where the heat exchanger is of vertical type, the gaseous 1,3,3,3-tetrafluoropropene is preferably introduced from the top side of the heat exchanger. In this case, the freezing of the water vapor occurs to cause a blockage from the top side of the heat transfer surface of the heat exchanger. It is thus desirable to provide a plurality of introduction holes in the bottom side of the heat exchanger and change the position of introduction of the crude 1,3,3,3-tetrafluoropropene gas to the bottom side. Even in the case where the heat exchanger is of horizontal type, the gaseous 1,3,3,3-tetrafluoropropene is also preferably introduced from the top side of the heat exchanger. A plurality of introduction holes may be provided in a line.

There is no particular limitation, on the dehydration temperature in the dehydration process of the present invention. For dehydration of the 1,3,3,3-tetrafluoropropene, the gaseous 1,3,3,3-tetrafluoropropene (boiling point: −19° C. at atmospheric pressure) needs to be cooled to a temperature at which it is condensed under operation pressure conditions. Such a temperature is −50 to −20° C., preferably −40 to −25° C., under atmospheric pressure conditions. If the temperature is higher than −20° C., it is difficult to condense the 1,3,3,3-tetrafluoropropene. It is impractical to cool the 1,3,3,3-tetrafluoropropene to a temperature lower than −50° C. due to the need for large-scale cooling equipment.

In a plant, a receiving tank is disposed on the bottom side of the heat exchanger so as to, when the crude 1,3,3,3-tetrafluoropropene is liquefied by condensation for freezing and removal of the water, receive and recover the liquefied crude 1,3,3,3-tetrafluoropropene in the receiving tank. The temperature of the receiving tank is preferably lower than or equal to the condensation temperature of the 1,3,3,3-tetrafluoropropene (boiling point: −19° C. at atmospheric pressure). Further, a U-shaped or coil-shaped tube may be disposed in the receiving tank so as to cool the receiving tank for further freezing and removal of the water in the liquefied crude 1,3,3,3-tetrafluoropropene.

There is no particular limitation on the cooling medium used in the heat exchanger in the dehydration process of the present invention. The cooling medium can be selected from an inorganic brine, which contains an aqueous medium and calcium chloride etc. as main ingredients, and an organic brine, which contains ethylene glycol or propylene glycol etc. as main ingredient, depending on the cooling temperature.

Furthermore, the heat of vaporization of the liquefied 1,3,3,3-tetrafluoropropene may be used as the cooling means. It is conceivable, in the case where the dehydration process of the present invention is applied to the dehydration step before the distillation step in the production of 1,3,3,3-tetrafluoropropene, to the vaporize the liquefied 1,3,3,3-tetrafluoropropene and then feed the vaporized 1,3,3,3-tetrafluoropropene to a distillation column of the distillation step. The load of heating and heat removal of external heating source can be removed for energy conservation when the liquefied 1,3,3,3-tetrafluoropropene is vaporized on the cooling-medium-flow side of the heat exchanger dehydration equipment.

In the dehydration process of the present invention, the pressure inside the heat exchanger during the dehydration of the 1,3,3,3-tetrafluoropropene is generally preferably 0.1 MPa or higher and 1 MPa or lower. The cooling temperature under such pressurized conditions can be set as appropriate depending on the pressure.

When the flow system is adopted for the heat exchanger, the linear velocity of the crude 1,3,3,3-tetrafluoropropene gas containing the water to be dehydrated in the heat exchanger is 6 to 1200 m/hr, preferably 30 to 600 m/hr. If the linear velocity is lower than 6 m/hr, the heat exchange dehydration equipment becomes excessively large. If the linear velocity is higher than 1200 m/hr, the freezing of the water and the condensation of the organic matter becomes insufficient so that the load of the subsequent distillation step increases.

In the flow system, the amount of the frozen water adhered to the heat transfer surface of the heat exchanger dehydration equipment increases with the time of contact of the water-containing crude 1,3,3,3-tetrafluoropropene gas. It is thus necessary to melt and remove the frozen water after the lapse of a predetermined time period. As the means for melting and removing the frozen water, there can be used a technique of flowing dry air or nitrogen etc. (as a heating medium) of 5 to 200° C. through the dehydration equipment from the top side. The temperature of the dry air or nitrogen etc. may be set to a high temperature. It is however desirable that the temperature of the dry air or nitrogen etc. is 20 to 100° C. for less thermal stress load on equipment material and for energy conservation.

As the heating means for melting the frozen water, there can be used a technique of, while increasing the temperature of the cooling medium, allowing the cooling medium to flow as a heating medium through the portion of the heat exchanger in which the cooling medium has flowed. There can also be used a technique of discharging the cooling medium out of the portion of the heat exchanger in which the cooling medium has flowed and instead flowing a heating medium through that portion of the heat exchanger. At this time, the cooling medium and the heating medium are not limited to be the same material or different materials. Furthermore, there can be used a technique of flowing dry air or nitrogen as a heating medium through the portion of the heat exchanger in which the water-containing 1,3,3,3-tetrafluoropropene has flowed. The frozen water is discharged from the top or bottom side of the dehydration equipment in the form of water or water vapor.

The 1,3,3,3-tetrafluoropropene gas to which the dehydration process of the present invention is applied contains at least water, that is, contains not only water vapor but also entrained water in mist form. In the production of 1,3,3,3-tetrafluoropropene, the total content of the contained water and the entrained water in the 1,3,3,3-tetrafluoropropene product immediately after the acid removal step is 3000 ppm to 10 mass % in mass ratio units. The water content of the 1,3,3,3-tetrafluoropropene can be lowered to the order of 1300 ppm by passing the 1,3,3,3-tetrafluoropropene product through a gas-liquid separator such as a mist separator. In the dehydration process of the present invention, the water content of the 1,3,3,3-tetrafluoropropene can be lowered to less than 100 ppm by condensing and liquefying the gaseous 1,3,3,3-tetrafluoropropene containing water simultaneously with freezing the water and thereby separating and removing the water from the 1,3,3,3-tetrafluoropropene.

In the production of 1,3,3,3-tetrafluoropropene, the product of the reaction process contains an acidic component. It is thus necessary to perform an acid removal process for removing the acidic component by washing the product with water or aqueous basing solution and, in the case where a large amount of hydrogen fluoride is contained in the product, to perform an acid removal process for removing the acidic component by absorbing the hydrogen fluoride by contact with concentrated sulfuric acid, and then, washing the product with water or aqueous basic solution. The 1,3,3,3-tetrafluoropropene containing the impurities after the acid removal process as mentioned above is preferably dehydrated by the dehydration process of the present invention. By subjecting the 1,3,3,3-tetrafluoropropene from which the acidic component has been removed to the dehydration process with the use of the heat exchanger dehydration equipment, it is possible to dehydrate the 1,3,3,3-tetrafluoropropene to a water content of less than 100 ppm.

In the plant for production of 1,3,3,3-tetrafluoropropene, it is desirable in the case of dehydrating the 1,3,3,3-tetrafluoropropene to a lower water content that the 1,3,3,3-tetrafluoropropene is purified by distillation operation in the distillation step after subjected to the dehydration step by the dehydration process of the present invention, and then, further dehydrated by a conventional dehydration process with the use of a zeolite. In this case, the water content of the 1,3,3,3-tetrafluoropropene can be lowered to 1 to 20 ppm by finally passing the 1,3,3,3-tetrafluoropropene gas through a zeolite-packed dehydration column. As the water content of the 1,3,3,3-tetrafluoropropene has already been lowered to less than 100 ppm by the dehydration process of the present invention using the heat exchanger in the dehydration step, the zeolite-packed dehydration column does not need to be large-scale equipment. It is more than adequate to use the zeolite-packed dehydration column of small size.

2. Synthesis of 1,3,3,3-Tetrafluoropropene

In general, the 1,3,3,3-tetrafluoropropene can be obtained by fluorinating 1-chloro-3,3,3-trifluoropropene with hydrogen fluoride, and then, removing the hydrogen fluoride by washing. The resulting 1,3,3,3-tetrafluoropropene contains not only water but also a cis-isomer, a trans-isomer or a mixture of cis- and trans-isomer of unreacted 1-chloro-3,3,3-trifluoropropene as impurities. The dehydration process of the present invention is applicable for dehydration of the above-obtained 1,3,3,3-tetrafluoropropene.

The 1,3,3,3-tetrafluoropropene can be also obtained by dehydrofluorinating 1,1,1,3,3-pentafluoropropane and removing hydrogen fluoride, generated as a by-product of the defluorination, by washing. The resulting 1,3,3,3-tetrafluoropropene contains not only water but also unreacted 1,1,1,3,3-pentafluoropropane as impurities. The dehydration process of the present invention is applicable for dehydration of the above-obtained 1,3,3,3-tetrafluoropropene.

Herein, the 1,3,3,3-tetrafluoropropene is a compound having a double bond and thus can exist as cis- and trans-isomers. By the above synthesis reaction, the 1,3,3,3-tetrafluoropropene is obtained in the form of a cis-isomer or a trans-isomer or a mixture of cis- and trans-isomers. There is no particular problem in using the 1,3,3,3-tetrafluoropropene in any form in the dehydration process of the present invention.

The 1,3,3,3-tetrafluoropropene, after dehydrated by the dehydration process of the present invention, contains the impurities but can be purified to a high purity by distillation.

3. Continuous Production Method of 1,3,3,3-Tetrafluoropropene

The present invention provides, by the adoption of the above dehydration process, a production method of 1,3,3,3-tetrafluoropropene by which the 1,3,3,3-tetrafluoropropene can be produced continuously. Namely, the present production method includes: a first step for synthesizing 1,3,3,3-tetrafluoropropene; a second step for removing an acidic component such as hydrogen fluoride and hydrogen chloride from the synthesized 1,3,3,3-tetrafluoropropene gas; a third step for cooling the 1,3,3,3-tetrafluoropropene gas by a heat exchanger to condense at least the 1,3,3,3-tetrafluoropropene, while freezing water, and thereby dehydrate the 1,3,3,3-tetrafluoropropene; and a fourth step for purifying the 1,3,3,3-tetrafluoropropene by distillation.

The above steps will be explained below one by one.

3.1 First Step: Synthesis of 1,3,3,3-Tetrafluoropropene

There is no particular limitation on the reaction process for synthesis of the 1,3,3,3-tetrafluoropropene as long as the resulting product of the reaction process contains the acidic component that needs to be removed by washing with water or aqueous basic solution etc. The following synthesis reaction processes can be adopted.

It is feasible to synthesize the 1,3,3,3-tetrafluoropropene by fluorination of a halogenohydropropene of the general formula: $CF_YCl_{3-Y}CH=CHF_WCl_{1-W}$ (where W is 0 or 1; and Y is an integer of 0 to 3 except for the case of W=1 and Y=3) with hydrogen fluoride. Examples of the halogenohydropropene, which forms 1,3,3,3-tetrafluoropropene by fluorination with hydrogen fluoride, are 1-chloro-3,3,3-trifluoropropene ($CF_3CH=CHCl$), $CF_2ClCH=CHF$ and $CFCl_2CH=CHF$.

For example, the 1,3,3,3-tetrafluoropropene can be synthesized by reaction of 1-chloro-3,3,3-trifluoropropene ($CF_3CH=CHCl$) with hydrogen fluoride. Although the reaction proceeds in either a liquid phase or a gas phase, it is industrially preferable to carry out the reaction in a gas phase for easy continuation of the reaction. In the case where the 1,3,3,3-tetrafluoropropene is synthesized in a gas phase in the presence of a fluorination catalyst, there can be adopted a synthesis process that uses activated carbon supporting thereon an oxide, a fluoride, a chloride, a fluorochloride, an oxyfluoride, an oxychloride or an oxyfluorochloride of one kind of metal, or two or more kinds of metals, selected from the group consisting of chromium, titanium, aluminum, manganese, nickel and cobalt as the fluorination catalyst (see Patent Document 1), or a synthesis process that uses at least one of titanium and chromium as the fluorination catalyst (see Patent Document 2)

It is also feasible to synthesize the 1,3,3,3-tetrafluoropropene by dehydrofluorination of 1,1,1,3,3-pentafluoropropane. In this case, the reaction is preferably carried out in the presence of a hydroxide of an alkali metal etc.

It is feasible to synthesize the 1,3,3,3-tetrafluoropropene by thermal decomposition reaction of 1,1,1,3,3-pentafluoropropane in the presence of a catalyst. There is no particular limitation on the thermal decomposition reaction. The thermal decomposition reaction can be either thermal cracking or catalytic cracking using alumina, zirconia, carbon material or catalyst in which aluminum, chromium etc. is supported on alumina, zirconia or carbon material. The thermal decomposition reaction is generally carried out in a gas phase at an elevated temperature under pressurized or reduced pressure conditions. The thermal decomposition reaction may be conducted with the use of a solvent inert to the hydrogen fluoride, such as fluorocarbon, hydrofluorocarbon or hydrocarbon, or an inert gas such as argon or nitrogen. For example, a mixed gas of the 1,3,3,3-tetrafluoropropene and hydrogen fluoride can be obtained as a reaction product by passing 1,1,1,3,3-pentafluoropropane through chromium-supported activated carbon at a temperature of 200 to 600° C. (see Patent Document 3). Further, a mixed gas of 1,1,1,2,3-pentafluoropropene and hydrogen fluoride can be obtained as a reaction product by passing 1,1,1,2,3,3-hexafluoropropane through activated carbon at a temperature of 200 to 600° C. (see Patent Document 5).

As the 1,3,3,3-tetrafluoropropene is a compound having a double bond, there exist cis and trans isomers of the 1,3,3,3-tetrafluoropropene as mentioned above. In any of the above synthesis processes, the 1,3,3,3-tetrafluoropropene is obtained as a cis-trans isomer mixture. There would be no particular problem in the use of such a mixture in the present manufacturing method. In practice, the 1,3,3,3-tetrafluoropropene is synthesized as a cis-trans isomer mixture by the reaction so that the resulting reaction product (crude 1,3,3,3-tetrafluoropropene gas) contains not only such a cis-trans isomer mixture of 1,3,3,3-tetrafluoropropene but also the raw material impurity such as unreacted 1-chloro-3,3,3-trifluoropropene (cis and trans isomers) or 1,1,1,3,3-pentafluoropropane and the acidic component impurity such as hydrogen fluoride or hydrogen fluoride.

3.2 Second Step: Acid Removal

As the crude 1,3,3,3-tetrafluoropropene obtained by any of the above synthesis reaction processes contains the acidic component as mentioned above, there is a need to remove the acidic component.

In the case where the hydrogen fluoride is contained in a large amount, it is necessary to perform an acid removal process for absorbing the hydrogen fluoride by contact with concentrated sulfuric acid and washing the resulting crude product with water or aqueous basic solution as mentioned above. Namely, the 1,3,3,3-tetrafluoropropene is extracted from the reactor in liquid form or gaseous form together with the hydrogen chloride and hydrogen fluoride, and then, subjected to the acid removal process. In the acid removal process, the acidic component such as hydrogen chloride and hydrogen fluoride is removed by liquid phase separation, sulfuric acid absorption and washing with water or aqueous basic solution. The crude 1,3,3,3-tetrafluoropropene is then subjected to the dehydration process after the acid removal process.

There is no particular limitation on the reagent used for removal of the hydrogen fluoride. For example, the hydrogen fluoride can be separated by formation of a complex with potassium fluoride, sodium fluoride etc. The hydrogen fluoride can be removed from the crude propene product by fixing the fluorine as calcium fluoride ($CaF_2$) by reaction with calcium chloride, calcium hydroxide, calcium oxide, calcium carbonate or aqueous solution thereof. Further, the hydrogen fluoride can be removed by reacting the hydrogen fluoride with alkali metal salt such as sodium chloride or potassium chloride and thereby fixing the fluorine as the corresponding metal fluoride salt.

In the case of removing a large amount of hydrogen fluoride in the plant, however, it is preferable to remove the hydrogen fluorine by contact with the sulfuric acid. When the hydrogen fluoride is brought into contact with the sulfuric acid, the amount of the sulfuric acid used depends on the amount of the hydrogen fluoride contained in the reaction mixture and can be adjusted as appropriate by any skilled in the art. It is feasible to determine the minimum required amount of the sulfuric acid from the solubility of hydrogen fluoride in 100% sulfuric acid with reference to a graph showing the solubility of hydrogen fluoride in sulfuric acid relative to the temperature (for example, about 34 g of hydrogen fluoride can be dissolved in 100 g of 100% sulfuric acid at 30° C.).

There is no particular limitation on the purity of the sulfuric acid. The purity of the sulfuric acid is preferably 50 mass % or higher, more preferably 98 to 100 mass %. In ordinary cases, there can be used commercially available industrial sulfuric acid (98 mass %).

This treatment process can be performed at a temperature that the reaction product does not become liquefied. The treatment temperature is generally 20 to 100° C., preferably 25 to 50° C., more preferably 25 to 40° C.

The hydrogen fluoride absorbed by the sulfuric acid can be recovered by distillation and recycled.

After the absorption of the hydrogen fluoride by the sulfuric acid, the hydrogen chloride that has not been absorbed by the sulfuric acid can be removed by absorption by any appropriate medium such as water.

3.3 Third Step: Dehydration

As the crude 1,3,3,3-tetrafluoropropene is brought into contact with the water or aqueous basic solution in the second step (acid removal step), a considerable amount of water is contained in the crude 1,3,3,3-tetrafluoropropene. The water content of the crude 1,3,3,3-tetrafluoropropene varies depending on the components and component ratio of the crude 1,3,3,3-tetrafluoropropene, the temperature conditions and the contact technique etc. Further, mist water is also entrained in the crude 1,3,3,3-tetrafluoropropene. The total content of the contained water and the entrained water in the crude 1,3,3,3-tetrafluoropropene is thus in the range of 3000 ppm to 10 mass % in mass unit. The dehydration process of the present invention is applicable even in such a case that the water content of the crude 1,3,3,3-tetrafluoropropene is high. It is however feasible to perform a preliminary dehydration process using a mist separator etc. so as to dehydrate the excessive entrained water in advance by cooling the crude 1,3,3,3-tetrafluoropropene at about 5° C. and condensing only the water. This preliminary dehydration process is effective when the water content of the crude 1,3,3,3-tetrafluoropropene exceeds 1% due to a large amount of entrained water. The mist separator may be of the type having a double tube packed with a metal, resin or inorganic packing material so as to, when the water-containing reaction product is fed through the double tube under low temperature conditions, remove the excessive water entrained in the product in an amount larger than or equal to the saturated water content. Further, the mist separator may be of centrifugal mist separation type or gravity mist separation type. The water content of the reaction product can be adjusted to 1000 to 2000 ppm by the above mist separator. By subjecting the crude 1,3,3,3-tetrafluoropropene from which the excessive water has been removed by the mist separator to the dehydration process of the present invention with the use of the heat exchanger, it is possible to lower the water content of the crude 1,3,3,3-tetrafluoropropene to 5 to 100 ppm simultaneously with condensing and liquefying the 1,3,3,3-tetrafluoropropene gas and the raw material gas.

3.4 Fourth Step: Distillation

Subsequently, the crude 1,3,3,3-tetrafluoropropene dehydrated by the dehydration process of the present invention is distillated by means of a distillation column so as to remove the raw material impurity and obtain either the cis isomer or trans isomer of the 1,3,3,3-tetrafluoropropene, i.e., purify the 1,3,3,3-tetrafluoropropene. For example, the trans-1,3,3,3-tetrafluoropropene can be obtained with a high purity of 99% or higher by controlling the distillation conditions for distillation of the crude 1,3,3,3-tetrafluoropropene by the distillation column after dehydrated by the dehydration process of the present invention.

As the boiling point (9° C.) of the cis-1,3,3,3-tetrafluoropropene is close to the boiling point (15° C.) of the 1,1,1,3,3-pentafluoropropane, the cis-1,3,3,3-tetrafluoropropene and the 1,1,1,3,3-pentafluoropropane are difficult to separate from each other by ordinary distillation operation. In the case where the cis-1,3,3,3-tetrafluoropropene and the 1,1,1,3,3-pentafluoropropane coexist, it is feasible to separate the cis-1,3,3,3-tetrafluoropropene and the 1,1,1,3,3-pentafluoropropane from each other by extractive distillation or to eliminate hydrogen fluoride from the 1,1,1,3,3-pentafluoropropane and thereby convert the 1,1,1,3,3-pentafluoropropane into trans-1,3,3,3-tetrafluoropropene or cis-1,3,3,3-tetrafluoropropene.

There is no particular limitation on the distillation column of the distillation process as long as the wall surface of the distillation column is inert to the distillate. The distillation column may be of the type having a wall surface formed of glass or stainless steel or of the type having a lining of tetrafluoroethylene resin, chlorotrifluoroethylene resin, vinylidene fluoride resin, tetrafluoroethylene-perfluoroalkylvinyl ether copolymer (PFA) resin or glass on a substrate of steel etc. Further, the distillation column may be packed with a packing material such as Raschig ring, Lessing ring, Pall ring or Saddle Sulzer packing. Although the distillation process can be carried out even at atmospheric pressure, it is preferable to carry out the distillation process under pressurized conditions for less pressure loss in the distillation column and for reduction of condenser load. There is no particular limitation on the number of stages of the distillation column required for the distillation process. The number of stages of the distillation column is preferably 5 to 100, more preferably 10 to 50. If the number of stages of the distillation column is less than 5, the purity of the trans-1,3,3,3-tetrafluoropropene may not be increased to a sufficient level. If the number of stages of the distillation column exceeds 100, there may occur the unfavorable problems that: the economical load of the distillation column itself increases; and the time required for the distillation process increases.

The dehydration process of the present invention can also be applied even in the case e.g. where the 1,3,3,3-tetrafluoropropene is subjected to washing after the distillation. Further, it is possible to lower the water content of the 1,3,3,3-tetrafluoropropene to 1 to 20 ppm or lower by, after the distillation, dehydrating the 1,3,3,3-tetrafluoropropene by the dehydration process of Patent Document 6 using the zeolite.

The dehydration process of the present invention may be performed with the use of a batch heat exchanger. It is however preferable to use the continuous flow heat exchanger in the dehydration process of the present invention in order to produce the 1,3,3,3-tetrafluoropropene continuously and efficiently for industrial commercial production in the plant.

4. Example of Dehydration of 1,3,3,3-Tetrafluoropropene

Figure 1:
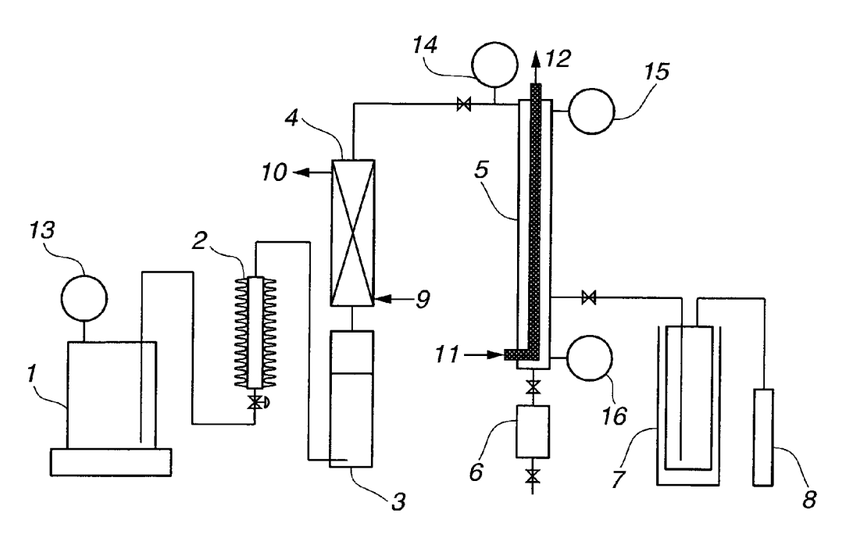
FIG. 1 shows a device example for dehydration of 1,3,3,3-tetrafluropropene according to one embodiment of the present invention.

An example of dehydration of 1,3,3,3-tetrafluoropropene by the dehydration process of the present invention will be explained below with reference to FIG. 1. In FIG. 1, reference numerals 13 and 14 designate pressure gauges; and reference numerals 15 and 16 designate thermometers.

In a cylinder 1, there is stored the crude 1,3,3,3-tetrafluoropropene containing the unreacted raw material, by-products, acidic component and water after the synthesis reaction of the 1,3,3,3-tetrafluoropropene. The crude 1,3,3,3-tetrafluoropropene is fed to and vaporized by a vaporizer 2. Subsequently, the crude 1,3,3,3-tetrafluoropropene is washed by a washing device 3 to remove the acidic component from the crude 1,3,3,3-tetrafluoropropene. The crude 1,3,3,3-tetrafluoropropene containing water vapor and mist after the acidic removal is fed through a mist separator 4. An aqueous ethylene glycol solution as a cooling medium is cooled at 5° C. and fed through the mist separator 4 from a cooling medium inlet port 9 to a cooling medium outlet port 10. With this, the water content of the crude 1,3,3,3-tetrafluoropropene is lowered by condensation of the water from the crude 1,3,3,3-tetrafluoropropene. The crude 1,3,3,3-tetrafluoropropene is then fed through a double-tube heat exchanger 5. Further, a cooling medium is fed from a cooling medium inlet port 11 to a cooling medium outlet port 12 through the heat exchanger 5. The crude 1,3,3,3-tetrafluoropropene and the impurities are thus cooled and condensed into a liquid, whereas the water is frozen onto an inner heat transfer surface of the heat exchanger 5.

The condensed crude 1,3,3,3-tetrafluoropropene liquid flows down from the double-tube heat exchanger 5 into a liquefied gas receiving tank 6 so that the crude 1,3,3,3-tetrafluoropropene accumulates in liquid form within the liquefied gas receiving tank 6.

The crude 1,3,3,3-tetrafluoropropene, if not liquefied by the double-tube heat exchanger 5, is fed in gaseous form to a chiller trap 7. In the chiller trap 7, a mixture of dry ice and acetone or liquid nitrogen is used as a cooling medium. As the cooling temperature of the chiller trap 7 is set lower than the cooling temperature of the double-tube heat exchanger 5, the crude 1,3,3,3-tetrafluoropropene gas that have not been liquefied by the double-tube heat exchanger 5 is condensed and collected by the chiller trap 7.

A drying agent-packed tube 8 is connected to a downstream side of the chiller trap 7 and is open to the air to prevent water in the air from entering the chiller trap 7 and the double-tube heat exchanger 5.

5. Comparison Between Dehydration Performance of Heat Exchanger and Zeolite-Packed Dehydration Column The following are the calculation results of the dehydration performance in the case of using as the dehydration equipment a heat exchanger as in the dehydration process of the present invention and in the case of using a dehydration column packed with a zeolite as the dehydration equipment. In either case, the dehydration performance was herein defined as, when the water content of the crude 1,3,3,3-tetrafluoropropene gas containing 1300 ppm water and unreacted raw material was lowered to 100 ppm, the mass of the crude 1,3,3,3-tetrafluoropropene dehydrated.

More specifically, a double-tube heat exchanger formed of SUS-316 with an outer tube inner diameter of 21.4 mm, an inner tube outer diameter of 8 mm, a length of 56 cm and an interior capacity of 201 cm$^3$ and a dehydration column formed with an inner diameter of 21.4 mm, a length of 35 cm and an interior capacity of 126 cm$^3$ and packed with spherical molecular sieve 3A of 2 mm in diameter as a zeolite were each tested for the dehydration performance at the time of dehydrating the crude 1,3,3,3-tetrafluoropropene containing 1300 ppm water and unreacted raw material to a water content of 100 ppm.

In the case of using the double-tube heat exchanger, the mass of the crude 1,3,3,3-tetrafluoropropene gas dehydrated by the time the dehydration performance of the heat exchanger was saturated was 30 kg.

By contrast, the mass of the crude 1,3,3,3-tetrafluoropropene gas dehydrated by the time the molecular sieve 3A of the dehydration tower was deactivated was 7.2 kg.

The following are formulas for calculation of the mass (kg/m$^3$) of the crude 1,3,3,3-tetrafluoropropene gas dehydrated per unit inner volume of the dehydration equipment (hereinafter referred to as "treatment amount") and the amount (kg/m$^3$) of dehydration per unit inner volume of the dehydration equipment.

Mass of crude 1,3,3,3-tetrafluoropropene gas dehydrated per unit inner volume of dehydration equipment (kg/m$^3$)=w×10$^6$/V Amount of dehydration per unit inner volume of dehydration equipment (kg/m$^3$)=(1300-100)×w/V In the above formulas, w is the mass (kg) of the crude 1,3,3,3-tetrafluoropropene gas that could be dehydrated to 100 ppm or lower; and V is the inner volume (cm$^3$) of the equipment.

By substituting w (30 kg as the mass of the crude 1,3,3,3-tetrafluoropropene gas dehydrated by the double-tube heat exchanger and 7.2 kg as the mass of the crude 1,3,3,3-tetrafluoropropene gas dehydrated by the dehydration column) into the above formulas, the treatment amount of the crude 1,3,3,3-tetrafluoropropene gas per unit inner volume of the dehydration equipment and the amount of dehydration per unit inner volume of the dehydration equipment were calculated. The calculation results are that: the treatment amount per 1 m$^3$ of the double-tube heat exchanger was 149×10$^3$ kg/m$^3$; treatment amount per 1 m$^3$ of the zeolite-packed dehydration column was 57×10$^3$ kg/m$^3$; the dehydration amount per 1 m$^3$ of the double-tube heat exchanger was 179 kg/m$^3$; and the dehydration amount per 1 m$^3$ of the zeolite-packed dehydration column was 69 kg/m$^3$.

It has been shown by the above calculation results that the dehydration performance of the double-tube heat exchanger in the dehydration process of the present invention was 2.6 times higher than that of the zeolite-packed dehydration column.

The double-tube heat exchanger not only has higher dehydration performance than the zeolite but also serves as a gas condenser so as to omit the use of a condenser and simplify the process for production of 1,3,3,3-tetrafluoropropene. The double-tube heat exchanger is thus suitably applicable for industrial plant use.

EXAMPLES

The present invention will be described in more detail below by way of the following examples. It should be noted that the following examples are illustrative and are not intended to limit the present invention thereto.

Example 1

Synthesis of 1,3,3,3-tetrafluoropropene

Provided was a tubular reactor formed of stainless steel (SUS-316) with an inner diameter of 23 mm and a length of 300 mm and capable of heating with a ribbon heater. The tubular reactor was charged with 50 ml of activated carbon supporting thereon chromium chloride (CrCl$_3$) as a catalyst. Then, hydrogen fluoride was fed into the tubular reactor at a feed rate of 0.2 g/min and at a temperature of 200° C. While feeding the hydrogen fluoride into the tubular reactor, the inside temperature of the tubular reactor was stepwise increased by 50° C. until it reached 400° C. The activation of the catalyst was performed in the temperature range of 200 to 400° C. over 8 hours in total.

The tubular reactor was heated in such a manner as to adjust the inside temperature of the tubular reactor to 320° C. After that, 1,1,1,3,3-pentafluoropropane was continuously fed into the tubular reactor at a feed rate of 0.8 g/min. In this state, the synthesis reaction of 1,3,3,3-tetrafluoropropene by defluorination of the 1,1,1,3,3-pentafluoropropane was continued for 100 hours.

Into a trap filled with water for acid absorption, the gas product of the reaction was bubbled to absorb and remove unreacted hydrogen fluoride. The resulting gas product was subjected to composition analysis by gas chromatography. The results of TABLE 1 were obtained. It has been shown by the composition analysis results that the reaction gas product contained 17.3 mass % unreacted 1,1,1,3,3-pentafluoropropane, 68.2 mass % synthesized trans-1,3,3,3-tetrafluoropropene, 14.4 mass % of synthesized cis-1,3,3,3-tetrafluoropropene and 0.1 mass % other components.

TABLE 1

| Components | Mass % |
|---|---|
| trans-1,3,3,3-tetrafluoropropene | 68.2 |
| cis-1,3,3,3-tetrafluoropropene | 14.4 |
| 1,1,1,3,3-pentafluoropropane | 17.3 |
| others | 0.1 |

[Dehydration Operation]

The thus-obtained gas was bubbled into water at 15 g/min and fed into a mist separator 4 as shown in FIG. 1, which was formed of SUS-316 and cooled by a cooling medium of 5° C., to remove entrained water from the gas. Herein, the mist separator 4 was packed with a packing material of SUS-316 in advance.

The gas discharged from the outlet port of the mist separator 4 was collected. The water content of the collected gas was determined by Karl Fischer technique to be 1300 ppm. Further provided was a double-tube heat exchanger 5 formed of SUS-316 with an outer tube inner diameter of 18 mm, an inner tube outer diameter of 8 mm and a length of 560 mm. The gas passed through the mist separator 4 was fed into a space between inner and outer tubes of the double-tube heat exchanger 5 at a feed rate of 15 g/min (linear velocity of 10 m/min in terms of gaseous form). At this time, the gas was introduced into the space between the inner and outer tubes of the double-tube heat exchanger 5 from the top side. A cooling medium of −40° C. was fed through the inner tube from an cooling medium inlet port 10 of the bottom side to a cooling medium outlet port 11 of the top side of the double-tube heat exchanger 5. Then, the gas was condensed and liquefied by cooling in the double-tube heat exchanger 5; and the water was frozen on a heat transfer surface of the outer side of the inner tube and removed.

The resulting liquefied gas product was discharged from the bottom side of the double-tube heat exchanger 5 and collected in a liquefied gas receiving tank 6. The water content of the collected liquefied product was determined by Karl Fischer technique to be 60 ppm. Further, the collected liquefied product was subjected to composition analysis by gas chromatography. The composition of the liquefied product was the same as that of FIG. 1.

[Distillation Operation]

The liquefied product was distilled by a distillation column etc. to extract and isolate the trans-1,3,3,3-tetrafluoropropene. The content rate of the trans-1,3,3,3-tetrafluoropropene was determined by Karl Fischer technique to be 90 ppm; and the purity of the trans-1,3,3,3-tetrafluoropropene was determined by gas chromatography to be 99.9%. By the distillation operation, 98 mass % of the trans-1,3,3,3-tetrafluoropropene in the gas was recovered.

Example 2

Synthesis of 1,3,3,3-tetrafluoropropene

Provided was a tubular reactor formed of stainless steel (SUS-316) with an inner diameter of 23 mm and a length of 300 mm and capable of heating with a ribbon heater. The tubular reactor was charged with 50 ml of chromium-supported alumina as a catalyst. Then, hydrogen fluoride was fed into the tubular reactor at a feed rate of 0.2 g/min and at a temperature of 200° C. While feeding the hydrogen fluoride into the tubular reactor, the inside temperature of the tubular reactor was stepwise increased by 50° C. until it reached 400° C. The activation of the catalyst was performed in the temperature range of 200 to 400° C. over 8 hours in total.

The tubular reactor was heated in such a manner as to adjust the inside temperature of the tubular reactor to 340° C. After that, trans-1-chloro-3,3,3-trifluoropropene was continuously fed into the tubular reactor at a feed rate of 0.16 g/min. On the other hand, hydrogen fluoride was also continuously fed into the tubular reactor at a feed rate of 0.24 g/min. In this state, the synthesis reaction of 1,3,3,3-tetrafluoropropene by fluorination of the trans-1-chloro-3,3,3-trifluoropropene with the hydrogen fluoride was continued for 10 hours.

Into a trap filled with water for acid absorption, the gas product of the reaction was bubbled to absorb and remove unreacted hydrogen fluoride and hydrogen chloride. The resulting gas product was subjected to composition analysis by gas chromatography. The results of TABLE 2 were obtained. It has been shown by the composition analysis results that the reaction gas product contained 40.4 mass % unreacted trans-1-chloro-3,3,3-trifluoropropene, 5.6 mass % cis-1-chloro-3,3,3-trifluoropropene, 33.0 mass % synthesized trans-1,3,3,3-tetrafluoropropene, 8.0 mass % of synthesized cis-1,3,3,3-tetrafluoropropene and 0.3 mass % other components.

TABLE 2

| Components | Mass % |
|---|---|
| trans-1,3,3,3-tetrafluoropropene | 33.0 |
| cis-1,3,3,3-tetrafluoropropene | 8.0 |
| trans-1-chloro-3,3,3-trifluoropropene | 40.4 |
| cis-1-chloro-3,3,3-trifluoropropene | 5.6 |
| 1,1,1,3,3-pentafluoropropane | 12.7 |
| others | 0.3 |

[Dehydration Operation]

The thus-obtained gas fed to the mist separator 4 and then the double-tube heat exchanger 5, both of which had been used in Example 1. Using these devices, the dehydration operation was conducted in the same manner as in Example 1. The resulting liquefied gas product was discharged from the bottom side of the double-tube heat exchanger 5 and collected in the liquefied gas receiving tank. The water content of the collected liquefied product was determined by Karl Fischer technique to be 60 ppm. Further, the collected liquefied product was subjected to composition analysis by gas chromatography. The composition of the liquefied product was the same as that of FIG. 2.

There was not found any new organic component as the purity organic component ratio was determined by gas chromatography to be the same as that of FIG. 2. Further, the distillation operation was performed in the same manner as in Example 1. By the distillation operation, 98 mass % of the trans-1,3,3,3-tetrafluoropropene in the gas was recovered.

As described above, it is possible in the dehydration process of the present invention to dehydrate 1,3,3,3-tetrafluoropropene by simple dehydration operation with the use of simple equipment and without the need to use large-scale equipment. This hydration process can suitably be applied for industrial commercial production of 1,3,3,3-tetrafluoropropene in a plant and enables continuous production of 1,3,3,3-tetrafluoropropene.

Although the present invention has been described with reference to the above specific embodiments, the present invention is not limited to these exemplary embodiments. Various modifications and variations of the embodiments described above can be made without departing from the scope of the present invention.

The invention claimed is:

1. A dehydration process of 1,3,3,3-tetrafluoropropene, comprising:
cooling the 1,3,3,3-tetrafluoropropene in gaseous form containing at least water by an indirect heat exchanger of either double-tube type, multi-cylinder type, cylindrical coil type or cylindrical jacketed type, thereby condensing and liquefying the 1,3,3,3-tetrafluoropropene while freezing and solidifying the water onto a heat transfer surface of the indirect heat exchanger.

2. The dehydration process according to claim 1, further comprising forming the 1,3,3,3-tetrafluoropropene in gaseous form containing at least water by fluorination of 1-chloro-3,3,3-trifluoropropene with hydrogen fluoride and then subjecting the 1,3,3,3-tetrafluoropropene to washing.

3. The dehydration process according to claim 2, wherein the 1,3,3,3-tetrafluoropropene contains at least a cis-isomer or a trans-isomer, or a mixture of cis- and trans-isomers, of the 1-chloro-3,3,3-trifluoropropene.

4. The dehydration process according to claim 1, further comprising forming the 1,3,3,3-tetrafluoropropene in gaseous form containing at least water by dehydrofluorination of 1,1,1,3,3-pentafluoropropane and then subjecting the 1,3,3,3-tetrafluoropropene to washing to remove impurities contained in the 1,3,3,3-tetrafluoropropene.

5. The dehydration process according to claim 4, wherein the 1,3,3,3-tetrafluoropropene contains at least the 1,1,1,3,3-pentafluoropropane as an impurity.

6. The dehydration process according to claim 1, wherein the 1,3,3,3-tetrafluoropropene is in the form of a cis-isomer or a trans-isomer or a mixture of cis- and trans-isomers thereof.

7. A production method of 1,3,3,3-tetrafluoropropene, comprising:

a dehydration step of dehydrating 1,3,3,3-tetrafluoropropene by the dehydration process according to claim 1; and a distillation purification step of distillating and purifying the dehydrated 1,3,3,3-tetrafluoropropene containing impurities.

8. The production method according to claim 7, further comprising:

a synthesis step for fluorinating 1-chloro-3,3,3-trifluoropropene with hydrogen fluoride to obtain a mixture of the 1,3,3,3-tetrafluoropropene, unreacted 1-chloro-3,3,3-trifluoropropene, hydrogen fluoride, hydrogen chloride and by-products; and an acid removal step for removing the hydrogen fluoride and hydrogen chloride from the mixture.

9. The production method according to claim 8, wherein, in the acid removal step, the hydrogen fluoride is removed by contact of the mixture obtained in the synthesis step with sulfuric acid, water or aqueous basic solution.

10. The production method according to claim 7, further comprising:

a synthesis step for dehydrofluorinating 1,1,1,3,3-pentafluoropropane to obtain a mixture of the 1,3,3,3-tetrafluoropropene, unreacted 1,1,1,3,3-pentafluoropropane and by-products; and an acid removal step for removing hydrogen fluoride from the mixture.

11. The production method according to claim 10, wherein, in the acid removal step, the hydrogen fluoride is removed by contact of the mixture obtained in the synthesis step with sulfuric acid, water or aqueous basic solution.

* * * * *